US00PP37348P2

(12) United States Plant Patent
Wagner et al.

(10) Patent No.: US PP37,348 P2
(45) Date of Patent: Mar. 31, 2026

(54) BLUEBERRY PLANT NAMED 'OBG-16252'

(50) Latin Name: ***Vaccinium virgatum* hybrid**
Varietal Denomination: OBG-16252

(71) Applicant: Robert Gabriel, Silverton, OR (US)

(72) Inventors: Adam L. Wagner, Brownsville, OR (US); D. Scott NeSmith, Griffin, GA (US)

(73) Assignee: Robert Gabriel, Silverton, OR (US)

( * ) Notice: Subject to any disclaimer, the term of this patent is extended or adjusted under 35 U.S.C. 154(b) by 0 days.

(21) Appl. No.: 19/187,745

(22) Filed: Apr. 23, 2025

(51) Int. Cl.
*A01H 5/08* (2018.01)

(52) U.S. Cl.
USPC ..... Plt./157

(58) Field of Classification Search
USPC ..... Plt./157
CPC . A01H 5/08; A01H 5/00; A01H 6/368; A01H 6/36
See application file for complete search history.

(56) References Cited

U.S. PATENT DOCUMENTS

PP23,374 P2 * 2/2013 NeSmith ..... A01H 5/08
Plt./157

OTHER PUBLICATIONS

Dowdy, New ornamental blueberries from UGA were bred for home landscapes, CAES Newswire 2019, retrieved on Jun. 10, 2025 at https://newswire.caes.uga.edu/story/8015/ornamental-blueberries.html, 4 pp. (Year: 2019).*

* cited by examiner

*Primary Examiner* — June Hwu
(74) *Attorney, Agent, or Firm* — Klarquist Sparkman, LLP

(57) ABSTRACT

A new and distinct blueberry plant variety named 'OBG-16252' is disclosed, characterized by its superior texture, large firm fruit with good flavor, exceptionally high yield, medium powder-blue color or bloom on the berry, and excellent vigor.

3 Drawing Sheets

Specification includes a Sequence Listing.

Latin name of the genus and species: *Vaccinium virgatum* hybrid.

Variety denomination: 'OBG-16252'.

INCORPORATION OF ELECTRONIC SEQUENCE LISTING

The Sequence Listing is submitted as an XML file named "Sequence.xml," created on Sep. 8, 2025 (16,656 bytes), which is incorporated herein by reference.

BACKGROUND

The present disclosure relates to a new and distinct *Vaccinium virgatum* (rabbiteye blueberry) hybrid variety named 'OBG-16252'. *Vaccinium virgatum* is of the family Ericaceae. 'OBG-16252' was first identified in a cultivated area in Silverton, Oregon, USA. The new variety is mid-season, has large berries, good flavor and firmness, with no observed notable diseases or other pest problems beyond those also common for other varieties, and a chilling requirement of approximately 500-600 hours below 45° F.

SUMMARY

'OBG-16252' is a product of a cross of 'T-959' (*Vaccinium virgatum* (*Vaccinium ashei*) female parent, U.S. Plant Pat. No. 24,135) and 'T-885' (*Vaccinium virgatum* (*Vaccinium ashei*) hybrid male parent, U.S. Plant Pat. No. 23,374). The new blueberry plant variety 'OBG-16252' has been asexually propagated (by vegetative cuttings) plantings in Silverton, Oregon, USA, where it was also established for testing and comparison to industry standards.

Asexual reproduction of this new variety by vegetative cuttings shows that the foregoing characteristics come true to form, are firmly fixed, and are established and transmitted through succeeding propagations.

The following traits have been repeatedly observed and are determined to be the unique and distinguishing characteristics of 'OBG-16252'. In combination, these traits set the new variety apart from all other existing varieties of rabbiteye blueberry known to the inventors:

1. Superior texture
2. Very large, firm fruit with good flavor
3. Exceptionally high yield
4. Medium powder-blue color or bloom on the berry
5. Excellent vigor In trials for the new variety in Silverton, Oregon, USA, standards 'T-959' and 'T-1101' were chosen for comparison as the most similar commercially available varieties. In addition, 'T-959' is the female parent.

'T-959' is credited as having superior texture and flavor for the species. For the sake of this application, texture is largely a reflection of seed abundance within each berry, and flavor is a subjective measure based on responses from taste panel participants. 'T-1101' (U.S. Plant Pat. No. 28,623) is a pollinator for 'T-959', though it suffers from higher berry seed count and non-distinct flavor, traits that have historically made the *Vaccinium virgatum* species less popular amongst consumers and growers. Both 'T-959' and 'OBG- 16252' are considered late season varieties, however 'OBG-16252' is ready to harvest approximately 7-10 days before 'T-959'.

Table 1 below shows a combination of subjective and objective measures that were used in the evaluation of 'OBG-16252' against the standards, 'T-1101' and 'T-959'. Subjective measures are rated on a scale of 1-10. Generally, flavor tends to reflect the panelists sensory perception of aroma as well as the balance of sugar and acid. Subjective measures of flavor are supplemented with objective data for soluble solids, pH, and titratable acidity. Texture is reflected through subjective panelist scores and is supported by the objective representation of seed counts.

TABLE 1

Comparison of 'OBG-16252' to 'T-1101' and female parent 'T-959'.

| | 'OBG-16252' | 'T-1101' | 'T-959' |
|---|---|---|---|
| Seed Abundance per Berry (avg) | 2 | 15 | 7 |
| Avg. Berry Size (mm) | 17.25 | 16.04 | 17.26 |
| Berry Flavor (per consumer panel) | 8 | 5 | 7 |
| Berry Texture (per consumer panel) | 9 | 3 | 7 |
| Avg. Soluble Solids (%) | 14.62 | 18.24 | 16.52 |
| Avg. pH | 3.16 | 3.54 | 3.32 |
| Avg.Titratable Acidity (% CA) | 0.51 | 0.26 | 0.36 |

The key improvements 'OBG-16252' offers to consumers include:

Better texture due to fewer seeds

Better flavor due to more pleasing aromatics and sugar/acid balance

Other improvements include:

Strong vigor

High yield

Large, firm berries

Excellent color

'OBG-16252' in an exceptional and unique new variety that will benefit the commercial blueberry industry.

The male parent ('T-885' U.S. Plant Pat. No. 23,374) was not selected for side-by-side comparison as it has limited commercial production value and is primarily used as an edible ornamental for home gardening. However, based on data provided in U.S. Plant Pat. No. 23,374, 'OBG-16252' can be distinguished from 'T-885' at least by the characteristics provided in Table 2.

TABLE 2

Comparison of 'OBG 16252' to 'T-885'.

| | 'T-885' | 'OBG 16252' |
|---|---|---|
| Berry Weight | 0.8-1.2 g | 3.19 g |
| Berry Height | 10-12 mm | 14.1 mm |
| Berry Diameter | 8.0-10 mm | 18 mm |
| Berry Surface | Non-glaucous | Glaucous |
| Foliage Surface | Non-glaucous | Glaucous |

BRIEF DESCRIPTION OF THE PHOTOGRAPHS

Figure 1:
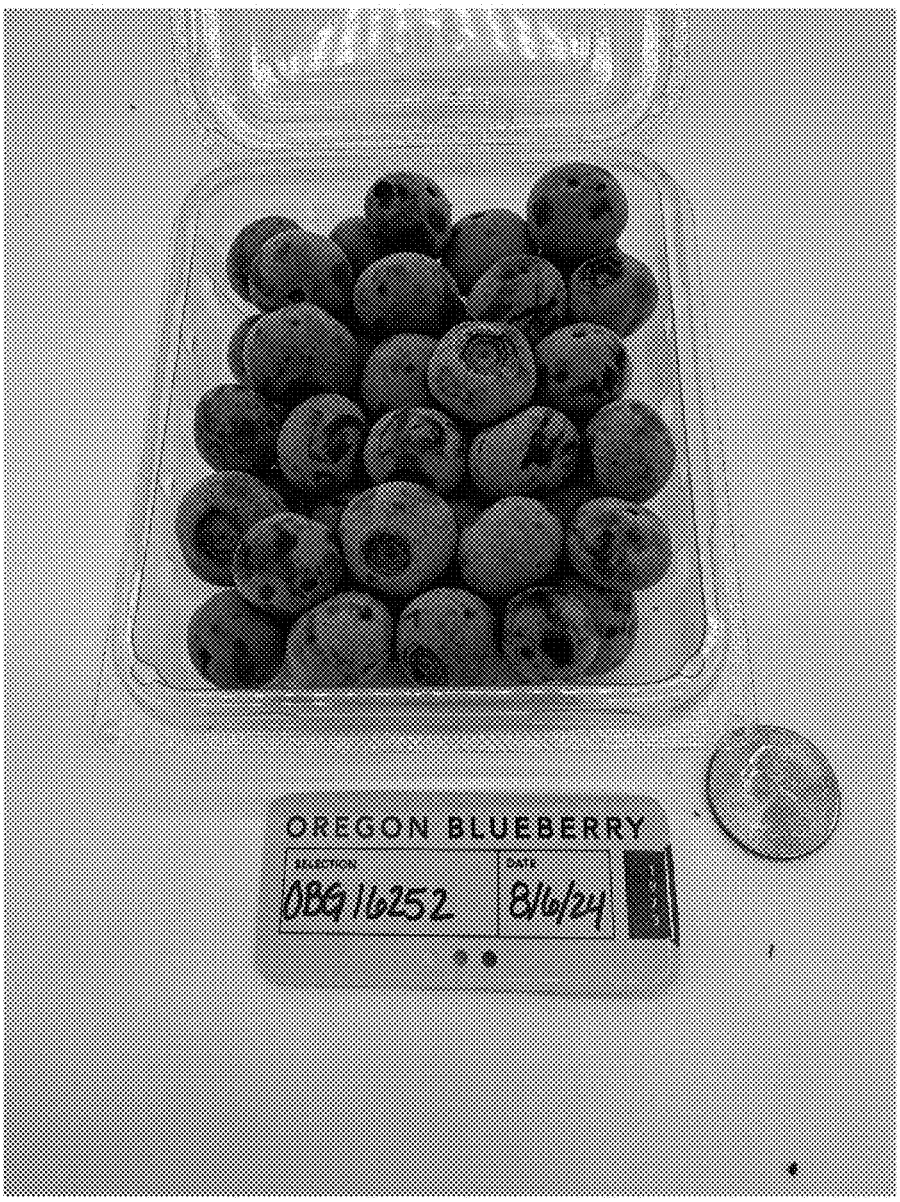
FIG. 1 is a photograph showing a close-up of 'OBG-16252' fruit in a packing clam shell. This photo was taken under artificial light in a photo tent at time of August 2023 harvest.
Figure 2:
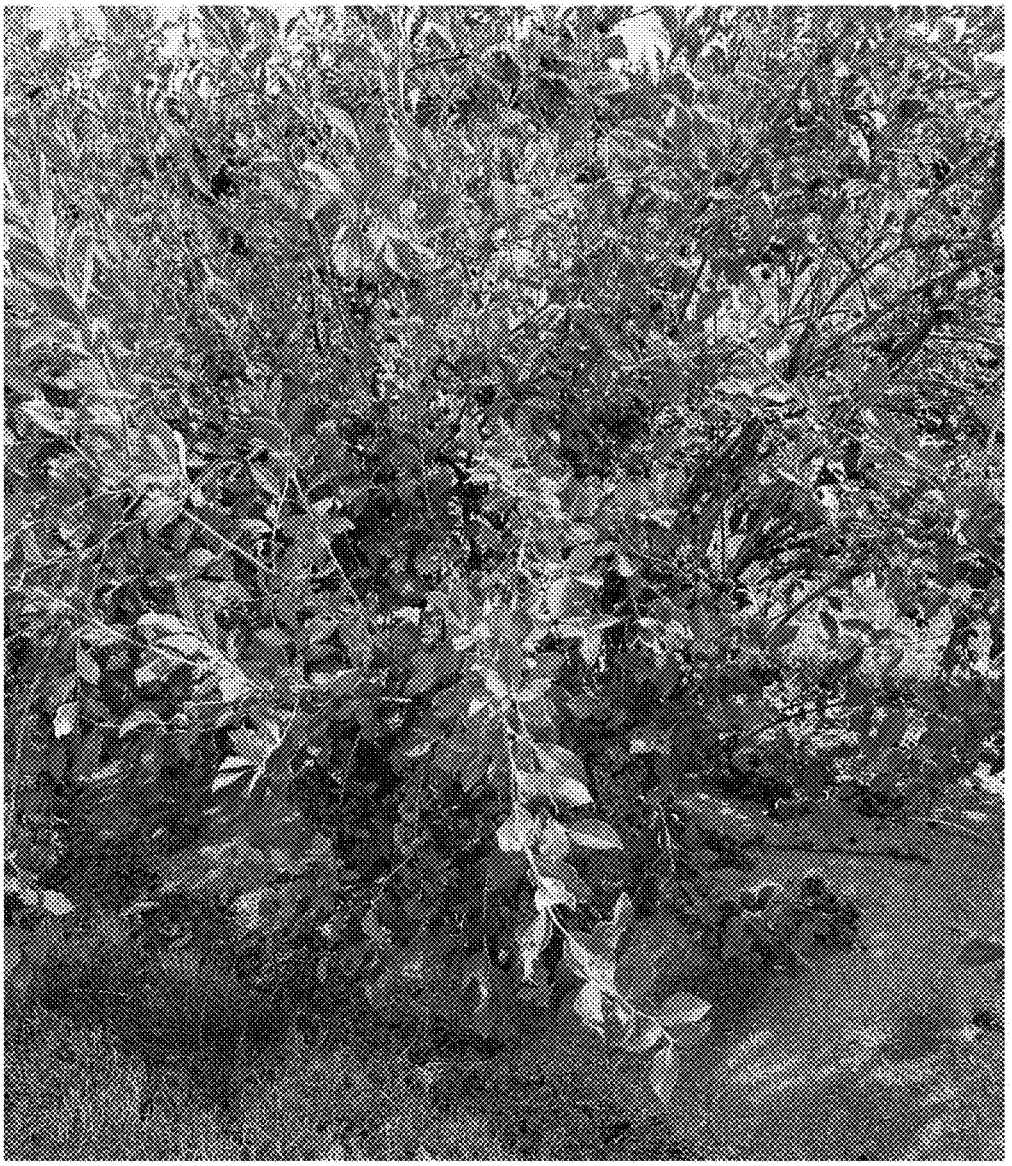
FIG. 2 is a photograph showing a four-year old 'OBG-16252' plant in ambient conditions outdoors in August 2023.
Figure 3:
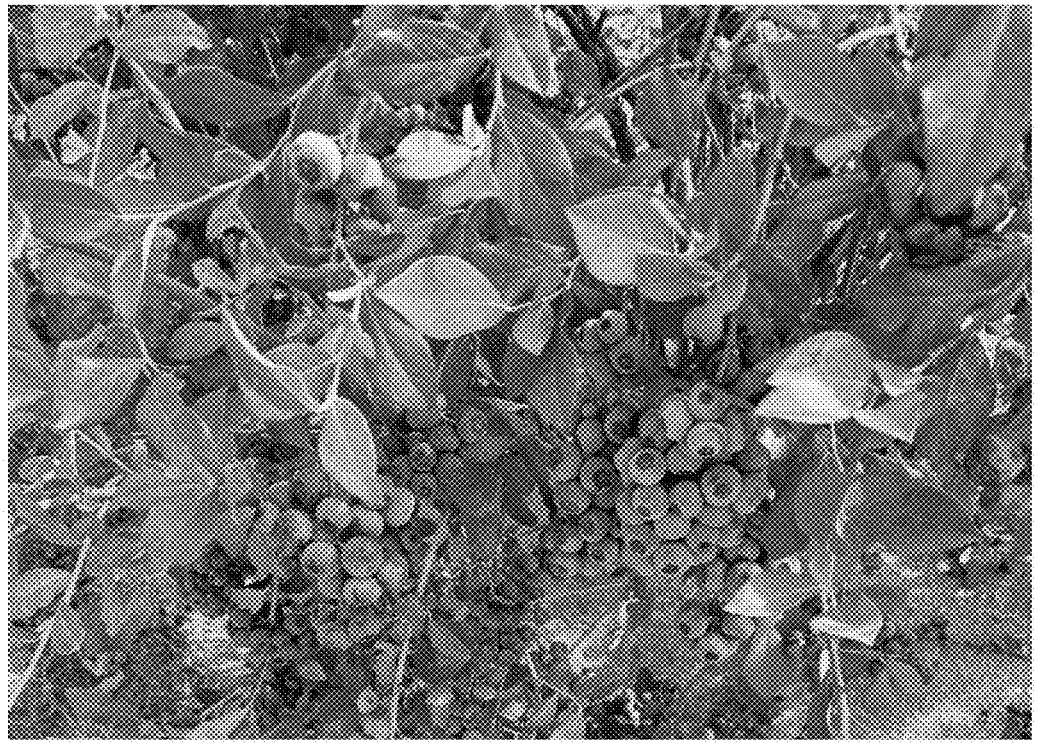
FIG. 3 is a photograph showing 'OBG-16252' fruit close-up on a 4 year-old plant in in ambient light conditions outdoors in August 2023.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED DESCRIPTION

Color descriptions and other terminology in this application are used in accordance with their ordinary dictionary descriptions, unless the context clearly indicates otherwise. Color designations (hue/value/chroma) are made with reference to The Royal Horticultural Society Colour Chart (R.H.S.), 5$^{th}$ edition, London, England, 2007.

The following detailed description of 'OBG-16252' is based on observations of asexually reproduced progeny 3-4 years of age. The following detailed description concerns plants growing in open fields with supplemental irrigation in Brooks, Oregon, USA. The average low temperature for the year ranges from 40-45° F., and the average high temperature of the year ranges from 90-95° F. The color values were determined in August 2023 under natural light conditions in Brooks, Oregon, USA.

'OBG-16252' has not been observed under all environmental conditions. Certain characteristics of this variety may change with changing environmental conditions such as photoperiod, temperature, moisture, soil conditions, nutrient availability, or other factors. Thus, the phenotype may vary somewhat with variations in environmental conditions without any variance in genotype.

Botanical classification: *Vaccinium virgatum* hybrid.

Common name: Rabbiteye blueberry.

Commercial classification: Fruit-bearing shrub.

Parentage:

*Female parent*.—'T-959' U.S. Plant Pat. No. 24,135.

*Male parent*.—'T-885' U.S. Plant Pat. No. 23,374.

Plant:

Plant size:

*Height*.—(cm): 165.1.

*Canopy diameter* (*cm*).—125.3. Growth Habit: Upright, Semi-bushy.

*Productivity* (*lbs/plant*).—3 Years Old: 5.4. 4 Years Old: 7.1.

*Degree of vigor*.—High.

Plant hardiness zone: USDA 6a-9a.

Suitability for mechanical harvesting: Good.

Evergreeness: Moderately High.

Foliage:

*Leaf color*.—Upper Surface: Green 131A. Lower Surface: Green 138A.

*Upper surface texture*.—Glaucous.

*Lower surface texture*.—Glaucous.

*Leaf arrangement*.—Alternate.

*Leaf shape*.—Elliptic to lanceolate.

*Leaf margin*.—Entire.

*Leaf venation*.—Pinnate.

*Leaf apices*.—Acute.
*Leaf bases*.—Cuneate.
Leaf dimensions:
*Length* (*mm*).—70.0 average.
*Width* (*mm*).—33.4 average.
*Attitude*.—Porrect.
Autumn foliage color: Tinted Greyed-Red 180A, Greyed Red 181A, Greyed Red 181B, Greyed-Red 178A, Green 131A.
Petiole:
*Length* (*mm*).—4.5 average.
*Width* (*mm*).—2.0 average.
*Color*.—Yellow-Green 144C, Red-Purple 58B.
*Surface texture*.—Glabrous.
Wood texture:
*New wood* (*June/July*).—Smooth, Glabrous.
1 *yr wood* (*August*).—Smooth, Glabrous.
3 *yr. wood* (*August*).—Rough, Exfoliating.
Wood color:
*New wood* (*June/July*).—Green 143C, Yellow-Green 144B.
1 *yr. wood* (*August*).—Yellow-Green 145A, tinted Red-Purple 60B when exposed to direct sun.
3 *yr, wood* (*August*).—Greyed-Orange 177A, Greyed-Orange 176A, Greyed-Orange 165A.
Wood buds:
*Average number of buds per fruiting lateral* (*in August*).—3.2.
Flowers:
Inflorescence/flowers:
*Flowering period*.—Mid to late April to late May.
*Time of beginning of flowering*.—Mid to late April.
*Time of* 50% *anthesis*.—Late April.
*Time of beginning of leaf bud burst*.—Mid April.
Inflorescence size:
*Length* (*mm*).—28.4 average.
*Width* (*mm*).—26.2 average.
*Flowering cluster density*.—Moderately tight.
*Number of flowers per cluster*.—6 average.
*Self-compatibility*.—80%.
Flower buds:
*Immature bud color*.—White NN155C tinted Greyed-Red 181C when exposed to direct sun.
*Mature bud color*.—White NN155C.
*Bud length* (*mm*).—11.9 average.
*Bud width* (*mm*).—5.8 average.
Flower pedicel:
*Color*.—Yellow-Green 144B tinted Greyed-Red 181B when exposed to direct sun.
*Length* (*mm*).—7.9 average.
*Texture*.—Smooth.
Flower peduncle:
*Color*.—Yellow-Green 144B tinted between Greyed-Red 180A and Red-Purple 60B.
*Length* (*mm*).—15.4 average.
Individual flower:
*Fragrance*.—No fragrance.
*Flower shape*.—Urceolate, round and slightly elongated.
*Flower length* (*mm*).—12.3 average.
*Protrusion of stigma beyond corolla* (*mm*).—0-0.1.
Calyx (with sepals):
*Outside color*.—Green 139D.
*Surface*.—Smooth.
*Diameter* (*mm*).—5.2 average.
Corolla:
*Color*.—White 155D.
*Length* (*mm*).—10.15 average.
*Width* (*mm*).—5.9 average.
*Aperture/width* (*mm*).—2.4 average.
*Anthocyanin coloration of corolla at time of anthesis*.—White NN155D.
*Texture*.—Smooth.
*Corolla ridges*.—Present.
Stamen:
*Length* (*mm*).—6.6 average.
*Number*.—10.
*Filament color*.—Yellow-Green 145C.
Anther:
*Length* (*mm*).—4.2 average.
*Number*.—10.
*Color*.—Greyed-Orange N167B.
Pollen:
*Staining*.—98%.
*Abundance*.—Moderate.
*Color*.—Yellow-White 158B.
Pistil:
*Length* (*mm*).—11.6 average.
*Ovary color* (*exterior*).—Green 137A.
*Style length* (*mm*).—9.4 average.
Fruit:
*Time of fruit ripening*.—Late July.
*Time of* 50% *maturity*.—Mid June.
*Fruit development period* (*#of days*).—81.
*Cluster density*.—High.
*Berry cluster*.—Moderately loose.
*Berries per cluster*.—8 average.
*Unripe berry color*.—Yellow-Green 144D, Yellow-Green 145C, Violet 84C.
*Ripe berry color*.—Near Violet-Blue 98D.
*Berry skin color after polishing*.—Blue 103A.
*Berry surface wax abundance*.—Moderately heavy and persistent.
*Berry flesh color*.—Near White N155D.
*Berry weight* (*g*).—3.19.
*Berry height from calyx to scar* (*mm*).—14.1.
*Berry diameter* (*mm*).—18.
*Calyx aperture* (*mm*).—9.0 average.
*Calyx depth* (*mm*).—0-0.25.
*Pedicel length* (*mm*).—10.5 average.
*Pedicel surface texture*.—Smooth.
*Berry attachment force*.—Moderate.
*Berry shape*.—Round/slightly oblate.
*Fruit stem scar*.—Medium, dry.
*Berry flavor*.—Excellent sweet/tart balance.
*Berry sweetness when ripe*.—Sweet, Tart.
*Acidity*.—5.1% CA.
*Firmness when ripe*.—Firm.
*Berry shelf life*.—Up to 4 weeks.
*Internode length on strong new shoots* (*mm*).—16.
Seed:
*Seed color*.—Greyed-Orange 164A.
*Seed length* (*mm*).—1.8 average.
*Seed width* (*mm*).—1.3 average.
*Seed dry weight* (*mg*).—4.5.
*Quantity seeds per berry*.—2.
Disease/pest resistance/susceptibility:
*Root rot* (*Phytophthora cinnamomi*).—Does not appear to be overly susceptible.
*Stem blight* (*Botryosphaeria spp.*).—Undetermined.

*Phomopsis twig blight* (*Phomopsis vaccinii*).—Does not appear to be overly susceptible.

*Botryosphaeria stem canker* (*Botryosphaeria corticis*) .—Undetermined.

*Bacterial cane canker* (*Pseudomonas syringae*).—Does not appear to be overly susceptible.

*Botrytis blight* (*Botrytis cinerea*).—Does not appear to be overly susceptible.

*Leaf spot* (*Septoria spp.*).—Does not appear to be overly susceptible.

*Leaf rust* (*Naohidemyces vaccinii*).—Does not appear to be overly susceptible.

*Bud mites* (*Acalitus vaccinii*).—Undetermined.

Primary market use: Fresh, frozen and pureed fruit market.

Genetic Fingerprinting

2×4 mm leaf tissue punches were pooled together into a 2 ml tube. 1 cubic zirconia bead and 100 ul PVP lysis buffer was added. The sample was ground at 1400 RPM for 1 minute, after which 250 μls of additional PVP lysis buffer was added. The sample was incubated at 60° C. for 1 hour and DNA was extracted following AutoGenepure® speed extraction protocol. Nine microsatellite markers were then assayed by PCR reaction on the extracted DNA. The PCR product was diluted into a running buffer and subject to electrophoresis. Analysis was done using GeneMarker® software.

Variety differentiation is based on the amplified peaks of individual markers, which depend on the genetic makeup of the variety (See, e.g., Boches et al. "Genetic Diversity in the Highbush Blueberry Evaluated with Microsatellite Markers" *J. Amer. Soc. Hort. Sci.* 131 (5): 674-686, 2006). Each variety displays different peak patterns for each marker, creating a unique genetic "fingerprint." The unique genetic fingerprint for 'OBG-18064' is:

Marker 1: 290,296,299

Marker 2: 189,192

Marker 3: 216,232

Marker 4: 189,194

Marker 5: 110,113

Marker 6: 230,233,235,253

Marker 7: 380,390,396,398,400

Marker 8: 317,319,327,332

Marker 9: 106,109,112,115

TABLE 3

Primer pairs for marker detection.

| Marker # | Forward | Reverse |
|---|---|---|
| 1 | TCCTCGTTCTCTCCCTCTCA (SEQ ID NO: 1) | CGCTGAAGTTGGAGTCCTT (SEQ ID NO: 2) |
| 2 | TCAGACATGATTGGGGAGGT (SEQ ID NO: 3) | GGAATAATAGAGGCGGTGGA (SEQ ID NO: 4) |
| 3 | GTTAAGCTTTTAGATGAGTT GATGG (SEQ ID NO: 5) | AACCAGTCCCAGACCCAAAT (SEQ ID NO: 6) |
| 4 | CGCAATCGCTGCATAGTTTA (SEQ ID NO: 7) | GTTTAACGTTGCAACCAATTCCA (SEQ ID NO: 8) |
| 5 | TAGTGGAGGGTTTTGCTTGG (SEQ ID NO: 9) | ATCGAAGCGAAGGTCAAAGA (SEQ ID NO: 10) |
| 6 | CGCGTGAAAAACGACCTAAT (SEQ ID NO: 11) | ACTCGATCCCTCCACCTG (SEQ ID NO: 12) |
| 7 | CACCCATTTCACGGAATCTC (SEQ ID NO: 13) | ACTTGGTCGGGTGTTGTCTC (SEQ ID NO: 14) |
| 8 | TCTCTTTCCCTTTTCAAGTGG (SEQ ID NO: 15) | GTTTATGATGGAATTCCGAGTT TG (SEQ ID NO: 16) |
| 9 | GTTCATCCCAATGCAGAAGA AG (SEQ ID NO: 17) | GTTTCCTCTTGTGGGTTAGGGTT TCT (SEQ ID NO: 18) |

SEQUENCE LISTING

```
Sequence total quantity: 18
SEQ ID NO: 1            moltype = DNA  length = 20
FEATURE                 Location/Qualifiers
source                  1..20
                        mol_type = other DNA
                        organism = synthetic construct
SEQUENCE: 1
tcctcgttct ctccctctca                                          20

SEQ ID NO: 2            moltype = DNA  length = 19
FEATURE                 Location/Qualifiers
source                  1..19
                        mol_type = other DNA
                        organism = synthetic construct
SEQUENCE: 2
cgctgaagtt ggagtcctt                                           19

SEQ ID NO: 3            moltype = DNA  length = 20
FEATURE                 Location/Qualifiers
source                  1..20
                        mol_type = other DNA
                        organism = synthetic construct
SEQUENCE: 3
tcagacatga ttggggaggt                                          20

SEQ ID NO: 4            moltype = DNA  length = 20
```

-continued

```
FEATURE                 Location/Qualifiers
source                  1..20
                        mol_type = other DNA
                        organism = synthetic construct
SEQUENCE: 4
ggaataatag aggcggtgga                                                20

SEQ ID NO: 5            moltype = DNA  length = 25
FEATURE                 Location/Qualifiers
source                  1..25
                        mol_type = other DNA
                        organism = synthetic construct
SEQUENCE: 5
gttaagcttt tagatgagtt gatgg                                          25

SEQ ID NO: 6            moltype = DNA  length = 20
FEATURE                 Location/Qualifiers
source                  1..20
                        mol_type = other DNA
                        organism = synthetic construct
SEQUENCE: 6
aaccagtccc agacccaaat                                                20

SEQ ID NO: 7            moltype = DNA  length = 20
FEATURE                 Location/Qualifiers
source                  1..20
                        mol_type = other DNA
                        organism = synthetic construct
SEQUENCE: 7
cgcaatcgct gcatagttta                                                20

SEQ ID NO: 8            moltype = DNA  length = 23
FEATURE                 Location/Qualifiers
source                  1..23
                        mol_type = other DNA
                        organism = synthetic construct
SEQUENCE: 8
gtttaacgtt gcaaccaatt cca                                            23

SEQ ID NO: 9            moltype = DNA  length = 20
FEATURE                 Location/Qualifiers
source                  1..20
                        mol_type = other DNA
                        organism = synthetic construct
SEQUENCE: 9
tagtggaggg ttttgcttgg                                                20

SEQ ID NO: 10           moltype = DNA  length = 20
FEATURE                 Location/Qualifiers
source                  1..20
                        mol_type = other DNA
                        organism = synthetic construct
SEQUENCE: 10
atcgaagcga aggtcaaaga                                                20

SEQ ID NO: 11           moltype = DNA  length = 20
FEATURE                 Location/Qualifiers
source                  1..20
                        mol_type = other DNA
                        organism = synthetic construct
SEQUENCE: 11
cgcgtgaaaa acgacctaat                                                20

SEQ ID NO: 12           moltype = DNA  length = 18
FEATURE                 Location/Qualifiers
source                  1..18
                        mol_type = other DNA
                        organism = synthetic construct
SEQUENCE: 12
actcgatccc tccacctg                                                  18

SEQ ID NO: 13           moltype = DNA  length = 20
FEATURE                 Location/Qualifiers
source                  1..20
                        mol_type = other DNA
                        organism = synthetic construct
SEQUENCE: 13
cacccatttc acggaatctc                                                20
```

-continued

```
SEQ ID NO: 14          moltype = DNA  length = 20
FEATURE                Location/Qualifiers
source                 1..20
                       mol_type = other DNA
                       organism = synthetic construct
SEQUENCE: 14
acttggtcgg gtgttgtctc                                              20

SEQ ID NO: 15          moltype = DNA  length = 21
FEATURE                Location/Qualifiers
source                 1..21
                       mol_type = other DNA
                       organism = synthetic construct
SEQUENCE: 15
tctctttccc ttttcaagtg g                                            21

SEQ ID NO: 16          moltype = DNA  length = 24
FEATURE                Location/Qualifiers
source                 1..24
                       mol_type = other DNA
                       organism = synthetic construct
SEQUENCE: 16
gtttatgatg gaattccgag tttg                                         24

SEQ ID NO: 17          moltype = DNA  length = 22
FEATURE                Location/Qualifiers
source                 1..22
                       mol_type = other DNA
                       organism = synthetic construct
SEQUENCE: 17
gttcatccca atgcagaaga ag                                           22

SEQ ID NO: 18          moltype = DNA  length = 26
FEATURE                Location/Qualifiers
source                 1..26
                       mol_type = other DNA
                       organism = synthetic construct
SEQUENCE: 18
gtttcctctt gtgggttagg gtttct                                       26
```

We claim:

1. A new and distinct variety of blueberry plant named ‘OBG-16252’, substantially as illustrated and described herein.

* * * * *